United States Patent
Sander et al.

(10) Patent No.: US 10,940,012 B2
(45) Date of Patent: Mar. 9, 2021

(54) TALAR DOME WITH ANGLED HOLES

(71) Applicant: Wright Medical Technology, Inc., Memphis, TN (US)

(72) Inventors: Elizabeth J. Sander, Memphis, TN (US); Kian-Ming Wong, Lakeland, TN (US); Braham K. Dhillon, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 16/297,940

(22) Filed: Mar. 11, 2019

(65) Prior Publication Data

US 2020/0289283 A1 Sep. 17, 2020

(51) Int. Cl.
*A61F 2/42* (2006.01)
*A61F 2/30* (2006.01)

(52) U.S. Cl.
CPC ........ *A61F 2/4202* (2013.01); *A61F 2/30771* (2013.01); *A61F 2002/30299* (2013.01); *A61F 2002/30774* (2013.01); *A61F 2002/4205* (2013.01); *A61F 2002/4207* (2013.01)

(58) Field of Classification Search
CPC ... A61F 2/24; A61F 2/2402; A61F 2002/4207
See application file for complete search history.

(56) References Cited

U.S. PATENT DOCUMENTS

| | | |
|---|---|---|
| 2004/0122523 A1 | 6/2004 | Guzman |
| 2009/0082875 A1 | 3/2009 | Long |
| 2013/0090739 A1 | 4/2013 | Linares et al. |
| 2016/0367270 A1 | 12/2016 | Garlock et al. |
| 2017/0304065 A1 | 10/2017 | Sanders et al. |
| 2018/0110625 A1 | 4/2018 | Dhillon et al. |

OTHER PUBLICATIONS

International Search Report and Written Opinion issued in connection with corresponding International Patent Application No. PCT/US2020/013470, dated Mar. 12, 2020, 12 pages.

*Primary Examiner* — Jason-Dennis N Stewart
(74) *Attorney, Agent, or Firm* — Duane Morris LLP

(57) ABSTRACT

A talar implant includes a post projecting from a superior surface of the plate and includes at least one threaded hole. A talar dome having an inferior surface is configured to face the plate and an opening in the inferior surface is shaped to receive the post. The talar dome includes at least one through hole having a threaded surface and a groove. The groove has a larger outer diameter than the threaded surface. At least one fastener is configured to engage the threaded hole of the post and the threaded surface of the through hole. The at least one fastener has a groove that is aligned with the groove of the through hole when the fastener is inserted in the talar dome and the post. At least one clip is configured to engage the groove of the through hole of the talar dome and the groove of the fastener.

14 Claims, 8 Drawing Sheets

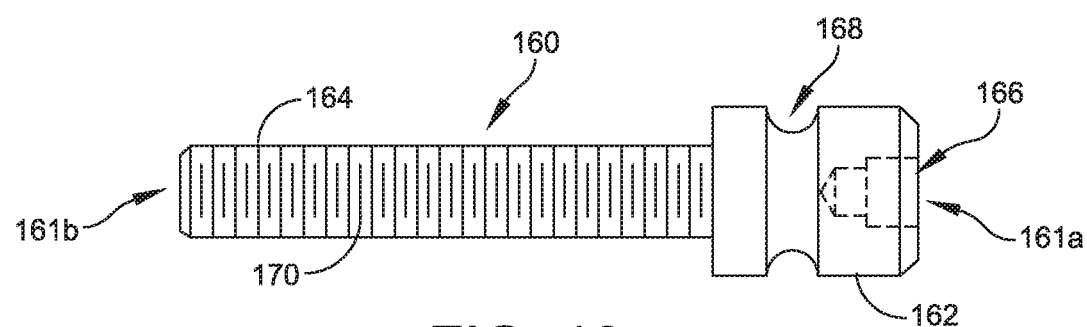
FIG. 13
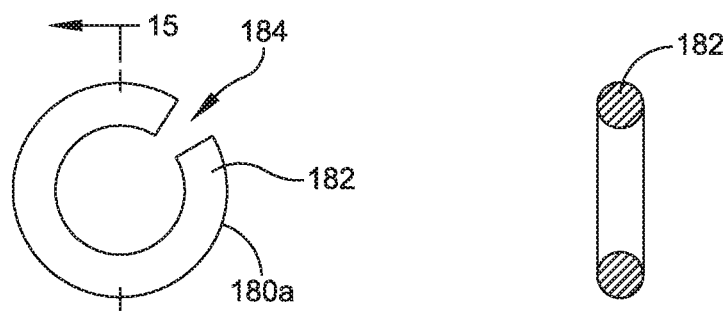
FIG. 14
FIG. 15
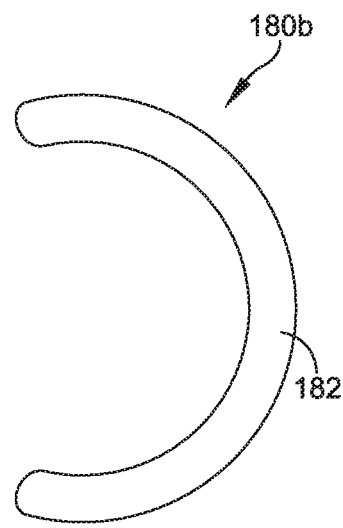
FIG. 16

TALAR DOME WITH ANGLED HOLES

BACKGROUND

An ankle joint may become severely damaged and painful due to arthritis, prior ankle surgery, bone fracture, osteoarthritis, and/or one or more additional conditions. Options for treating the injured ankle have included anti-inflammatory and pain medications, braces, physical therapy, joint arthrodesis, and total ankle replacement.

Total ankle replacement generally comprises two components—one component coupled to the tibia and one component coupled to the talus. The components comprise articulation surfaces sized and configured to mimic the range of motion of the ankle joint. For example, the talar portion may comprise a component sized and configured to mimic the talar dome and the tibial portion may comprise an articulation surface configured to mimic articulation of the tibia.

SUMMARY

In various embodiments, a talar implant is disclosed. The talar implant includes a plate having an inferior surface configured for attachment to a talus. The plate has a post projecting from a superior surface of the plate and includes at least one threaded hole. A talar dome having an inferior surface is configured to face the plate and an opening in the inferior surface is shaped to receive the post. The talar dome includes at least one through hole having a threaded surface and a groove. The groove has a larger outer diameter than the threaded surface. At least one fastener is configured to engage the threaded hole of the post and the threaded surface of the through hole. The at least one fastener has a groove that is aligned with the groove of the through hole when the fastener is inserted in the talar dome and the post. At least one clip is configured to engage the groove of the through hole of the talar dome and the groove of the fastener.

In various embodiments, an ankle prosthesis is disclosed. The ankle prosthesis includes a tibial component configured for attachment to a tibia of a person, a plate having an inferior surface configured for attachment to a talus of the person, and a talar dome. The plate includes a post projecting from a superior surface of the plate and defines first and second threaded holes. The talar dome includes an articulating surface configured to face the tibial component, an inferior surface configured to face the plate, and an opening in the inferior surface shaped to receive the post. The talar dome defines first and second through holes having respective first and second threaded surfaces with a diameter and first and second grooves, respectively. The first and second grooves have an outer diameter larger than the diameter of the first and second threaded surfaces. First and second fasteners are configured to engage the first and second threaded holes, and the first and second threaded surfaces of the talar dome, respectively. The first and second fasteners each have a groove that is aligned with the first and second grooves of the talar dome, respectively, when the first and second fasteners are inserted in the talar dome and the post. First and second clips are configured to engage the first and second grooves of the first and second through holes and the first and second grooves of the first and second fasteners, respectively.

In various embodiments, a method of inserting a talar implant is disclosed. The method includes attaching a plate to a talus so that an inferior surface of the plate abuts the talus. The plate includes a post projecting from a superior surface of the plate. The post includes at least one threaded hole. The method further includes placing a talar dome over the plate, so that an inferior surface of the talar dome abuts the plate, and an opening in the inferior surface of the talar dome receives the post, the talar dome having at least one through hole. The through hole includes a threaded surface and a groove. At least one fastener is inserted through the threaded surface of the through hole to engage the threaded hole of the post. The fastener includes a groove. At least one clip is inserted in the through hole, so as to engage the groove of the through hole of the talar dome and the groove of the fastener.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIG. 13 illustrates a fastener sized and configured to be inserted into a through hole of a talar dome, in accordance with some embodiments.

FIG. 14 illustrates a clip configured to be coupled to a fastener, in accordance with some embodiments.

FIG. 15 illustrates a cross-sectional view of the clip taken along line 15-15 in FIG. 14, in accordance with some embodiments.

FIG. 16 illustrates a C clip configured to be coupled to a fastener, in accordance with some embodiments.

DETAILED DESCRIPTION

Figure 1:
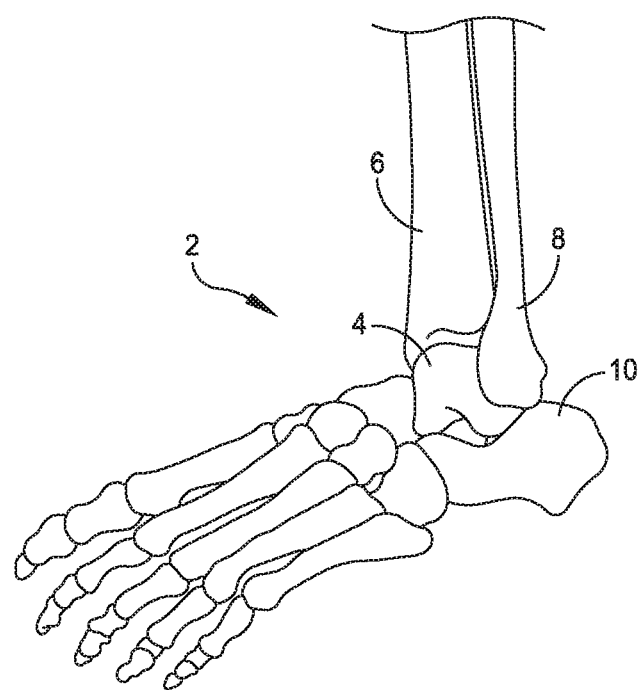
FIG. 1 illustrates an anatomic view of an ankle joint.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

In various embodiments, a talar implant is disclosed. The talar implant includes a plate having an inferior surface configured for attachment to a talus. The plate has a post projecting from a superior surface of the plate and includes at least one threaded hole. A talar dome having an inferior surface is configured to face the plate and an opening in the inferior surface is shaped to receive the post. The talar dome includes at least one through hole having a threaded surface and a groove. The groove has a larger outer diameter than the threaded surface. At least one fastener is configured to engage the threaded hole of the post and the threaded surface of the through hole. The at least one fastener has a groove that is aligned with the groove of the through hole when the fastener is inserted in the talar dome and the post. At least one clip is configured to engage the groove of the through hole of the talar dome and the groove of the fastener.

Figure 2:
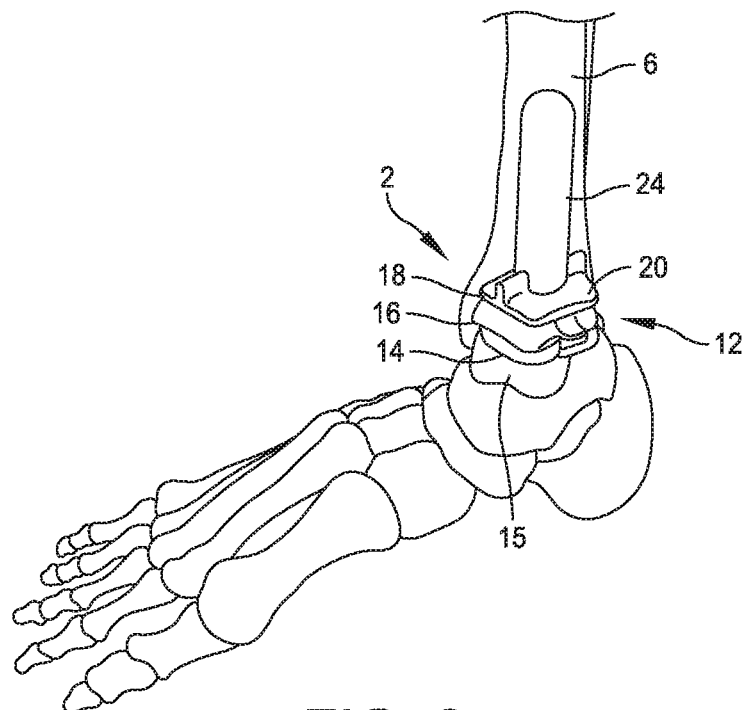
FIG. 2 illustrates one embodiment of an ankle joint having a total ankle replacement system therein, in accordance with some embodiments.

FIG. 1 illustrates an anatomic view of an ankle joint 2. The ankle joint 2 comprises a talus 4 in contact with a tibia 6 and a fibula 8. A calcaneus 10 is located adjacent to the talus 4. In total ankle replacements, the talus 4 and the tibia 6 may be resected, or cut, to allow insertion of a talar implant and a tibial implant. FIG. 2 illustrates the ankle joint 2 of FIG. 1 having a total ankle replacement system 12 inserted therein.

The total ankle replacement system 12 comprises a talar implant 14 and a tibial implant 18. The talar implant 14 includes a talar dome having a body defining a talar articulation surface 16. The talar implant 14 includes a plate coupled to the talus by one or more fasteners (not shown). The tibial implant 18 is sized and configured for installation into the tibia 6. The tibial implant 18 comprises a body having an articulation surface 20 and, in some embodiments, a tibial stem 24 extending into the tibia 6 to anchor the tibial implant 18. The talar joint surface 16 and the tibial joint surface 20 are mutually sized and configured to articulate. The joint surfaces 16, 20 replace the natural ankle joint surfaces, which are removed, to restore a range of motion that mimics the natural joint. One or more holes may be formed in the tibia and/or the talus prior to and during insertion of the tibial implant 18 or the talar implant 12. For example, in some embodiments, a hole is drilled starting in the bottom of the talus, extending through the talus and into the tibia. The hole may comprise, for example, a 6 mm hole configured to receive the stem 24 of the tibial implant 18.

The joint surfaces 16, 20 may be made of various materials, such as, for example, polyethylene, high molecular weight polyethylene (HMWPE), rubber, titanium, titanium alloys, chrome cobalt, surgical steel, and/or any other suitable metal, ceramic, sintered glass, artificial bone, and/or any combination thereof. The joint surfaces 16, 20 may comprise different materials. For example, the tibial joint surface 20 may comprise a plastic or other non-metallic material and the talar joint surface 16 may comprise a metal surface. Those skilled in the art will recognize that any suitable combination of materials may be used.

FIGS. 3-6 illustrate a talar implant 100 including a talar dome 110 and a talar plate 120, in accordance with some embodiments. The talar plate 120 includes a body 122 extending between an inferior surface 124 and a superior surface 126 and defined by a perimeter wall 128. The inferior surface 124 is sized and configured to contact a resected talus. For example, the inferior surface 124 may comprise a planar surface, a concave surface, and/or any desirably shaped surface configured to rest on the surface of a resected (or partially-resected) talus. In the illustrated embodiment, the inferior surface 124 includes a planar surface.

Figure 11:
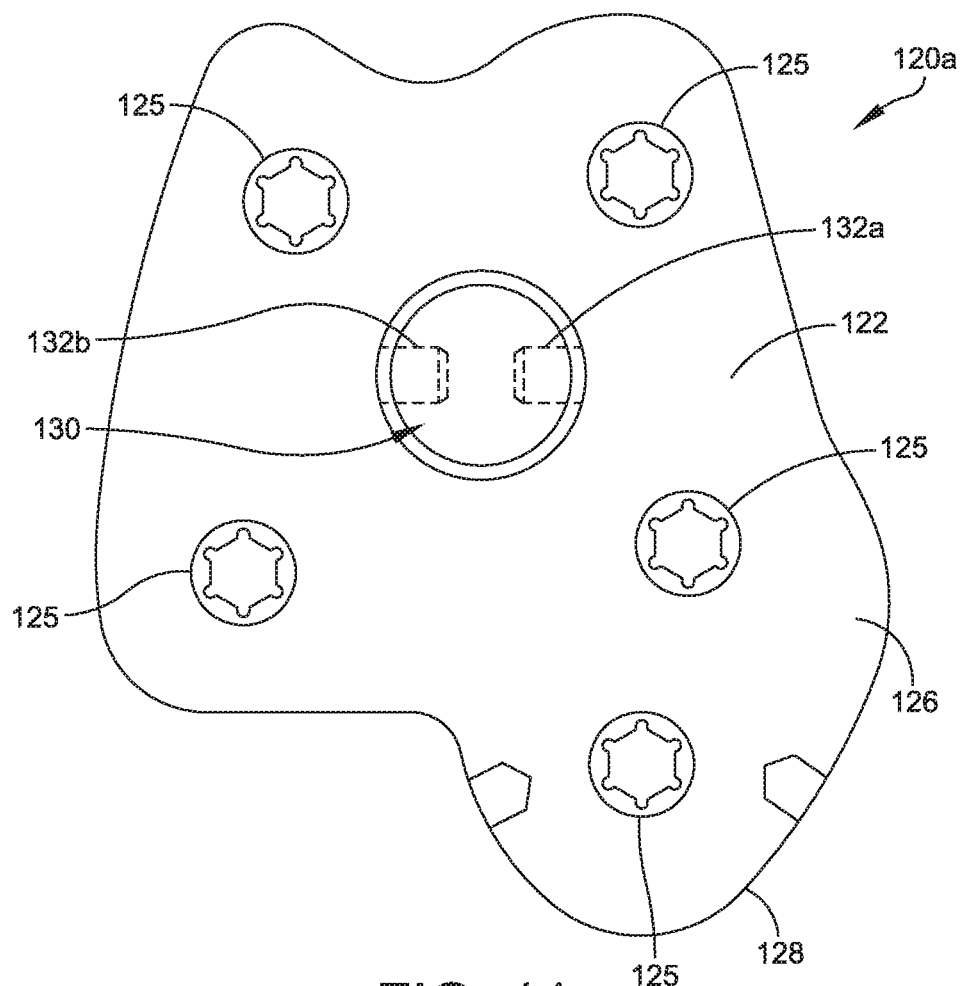
FIG. 11 illustrates a top view of a talar plate including a post configured to be coupled to a talar dome, in accordance with some embodiments.
Figure 12:
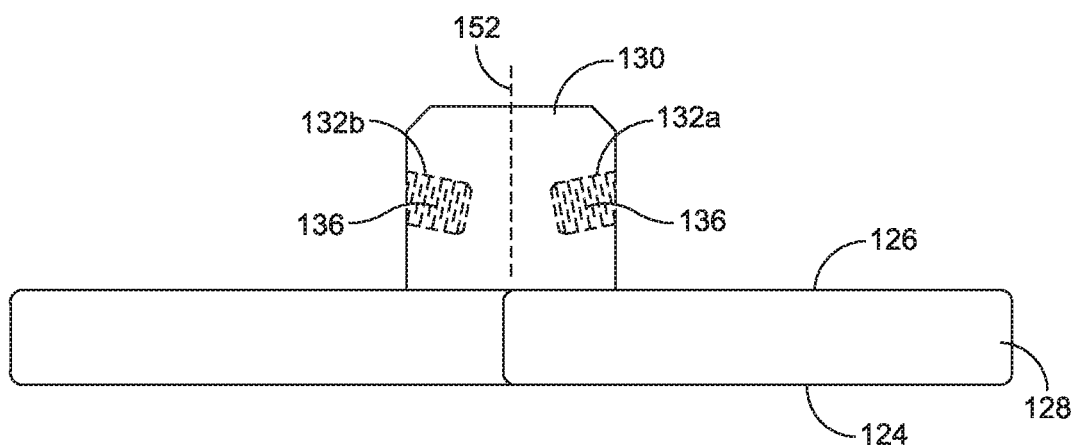
FIG. 12 illustrates a side view of the plate of FIG. 11, in accordance with some embodiments.

FIGS. 11-12 illustrate one embodiment of a talar plate 120a, in accordance with some embodiments. The body 122 defines a plurality of fastener holes 125 extending through the body 122 from the superior surface 126 to the inferior surface 124. The fastener holes 125 are sized and configured to receive a fastener therethrough to couple the talar plate 120 to a resected talus. In some embodiments, the fastener holes 125 are configured to receive a fastener at a variable angle with respect to a central axis of each of the fastener holes 125. In other embodiments, one or more fastener holes 125 are omitted and/or alternative or additional attachment mechanisms may be included, such as fixed pegs, spikes, and/or any other suitable attachment mechanism.

With reference now to FIGS. 3-6 and 11-12, in some embodiments, a post 130 extends from the superior surface 126 of the talar plate 120. The post 130 extends a predetermined distance above the superior surface 126. In the illustrated embodiment, the post 130 extends substantially perpendicular to the planar superior surface 126, although it will be appreciated that the post 130 can extend from the superior surface 126 at any suitable angle, such as, for example, an angle substantially between 45 and 90 degrees. The post 130 can include any suitable shape, such as, for example, a geometric (e.g., circular, cuboid, hexagonal, octagonal, etc.) or non-geometric shape. The post 130 may be formed integrally with the talar plate 120 and/or may be coupled to the talar plate 120 using any suitable coupling mechanism, such as a screw, pin, or other fastener.

In some embodiments, the post 130 defines one or more fastener holes 132a, 132b extending from an outer surface 134 of the post 130 at least partially into the post 130. Each of the one or more fastener holes 132a, 132b is sized and configured to receive a distal portion of a fastener, such as a screw, therein, as discussed in greater detail below. Each fastener hole 132a, 132b extends into the post 130 at a first angle with respect to a plane defined by one or more surfaces of the talar plate 120, such as, for example, a plane defined by the inferior surface 124, the superior surface 126, a distal end of the post 130, and/or any other suitable surface.

In some embodiments, the post 130 defines a central vertical axis 152 and each of the holes 132 extend into the post 130 such that a longitudinal axis of the hole 132 does not extend through the central vertical axis 152 of the post 130. For example, in some embodiments, a longitudinal axis of each of the holes 132a, 132b is offset or off-center within the post 130. The combination of the first angle and the offset may be referred to herein as a compound angle.

In some embodiments, each of the fastener holes 132a, 132b include an internal threading 136 configured to couple the post 130 to a distal portion of a threaded screw, as discussed in greater detail below. The fastener holes 132a, 132b may have similar and/or different internal threading. In some embodiments, the internal threading 136 is omitted and a fastener is coupled to the post 130 using an additional and/or alternative coupling mechanism, such as a cross-pin, an adhesive, and/or any other suitable coupling mechanism.

FIGS. 7-10 illustrate one embodiment of a talar dome 110a. With reference now to FIGS. 3-10, the talar dome 110, 110a includes a body 112 extending between a superior articulation surface 114 and an inferior plate contact surface 116. The body 112 has a predetermined thickness between the articulation surface 114 and the plate contact surface 116. The predetermined thickness can be constant and/or variable. The articulation surface 114 is sized and configured to interface with an opposing articulation surface of an opposing implant and/or bone structure. For example, in one embodiment, the articulation surface 114 is sized and configured to interface with an articulation surface of a tibial implant, such as, for example, the tibial implant 18 shown in FIG. 2. In another example, the articulation surface 114 is sized and configured to interface with an articulation body located between a tibial implant 18 and the talar dome 110, 110a, such as, for example, a poly insert defining an articulation surface.

In some embodiments, the plate contact surface 116 comprises a surface configured to contact a superior surface 126 of the talar plate 120. The plate contact surface 116 includes a surface complimentary to the superior surface 126 of the talar plate 120, such as, for example, a planar surface, concave surface, convex surface, etc. For example, in the illustrated embodiment, the plate contact surface 116 and the superior surface 126 each include generally planar surface. In various embodiments, the plate contact surface 116 can include dimensions that are greater than, less than, or equal to the dimensions of the superior surface 126 of the talar plate 120, such that the talar dome 110, 110a may extend less than, up to, and/or beyond the peripheral edge 128 of the talar plate 120.

In some embodiments, the talar dome 110, 110a defines a post hole 118 extending from the plate contact surface 116 into the body 114 of the talar dome 110, 110a. The post hole 118 is sized and configured to receive the post 130 of the talar plate 120 therein. The post hole 118 has a complimentary cross-sectional shape with respect to the post 130. For example, in some embodiments, post 130 defines a substantially geometric shape, such as, for example, a circle, square, hexagon, octagon, etc., and the post hole 118 defines a complimentary substantially geometric cross-section. In some embodiments, the post hole 118 and the post 130 include complimentary shapes configured to allow insertion of the post 130 into the post hole 118 only when the talar dome 110, 110a and the talar plate 120 are arranged in one or more predetermined alignments. For example, in some embodiments, the post 130 may define a trapezoidal shape such that the post 130 fits into the complimentary post hole 118 only when the short side of the post 130 is aligned with a short side of the post hole 118. Although specific examples are discussed herein, it will be appreciated that the post hole 118 and/or the post 130 can have any suitable shape and are within the scope of this disclosure.

In some embodiments, the post hole 118 includes a depth sufficient to receive the entire post 130 therein such that the plate contact surface 116 of the talar dome 110, 110a sits flush against the superior surface 126 of the talar plate 120. The post 130 may have a diameter such that a partial friction fit exists between the post hole 118 and the post 130 requires a force, such as a force applied by one or more fasteners to position the talar dome 110, 110a flush with the superior surface 126 of the talar plate 120.

The talar dome 110, 110a includes one or more through holes 140a, 140b each extending along a respective longitudinal axis 146a, 146b from the articulation surface 114 through an interior wall 142 of the post hole 118. The through holes 140a, 140b are sized and configured to receive a fastener therein (see FIG. 6). In some embodiments, each through hole 140a, 140b includes an internal thread 144 extending over at least a portion of the through hole 140a, 140b. The internal thread 144 is configured to couple a portion of a fastener, such as a screw, to the talar dome 110. In some embodiments, the internal thread 144 is substantially similar to the internal thread 136 of one or more holes 132 formed in the post 130 such that a fastener having a single thread can interact with each of the threads 136, 144 in each of a through hole 140a, 140b in a talar dome 110 and a fastener hole 132a, 132b in a post 130.

Figure 9:
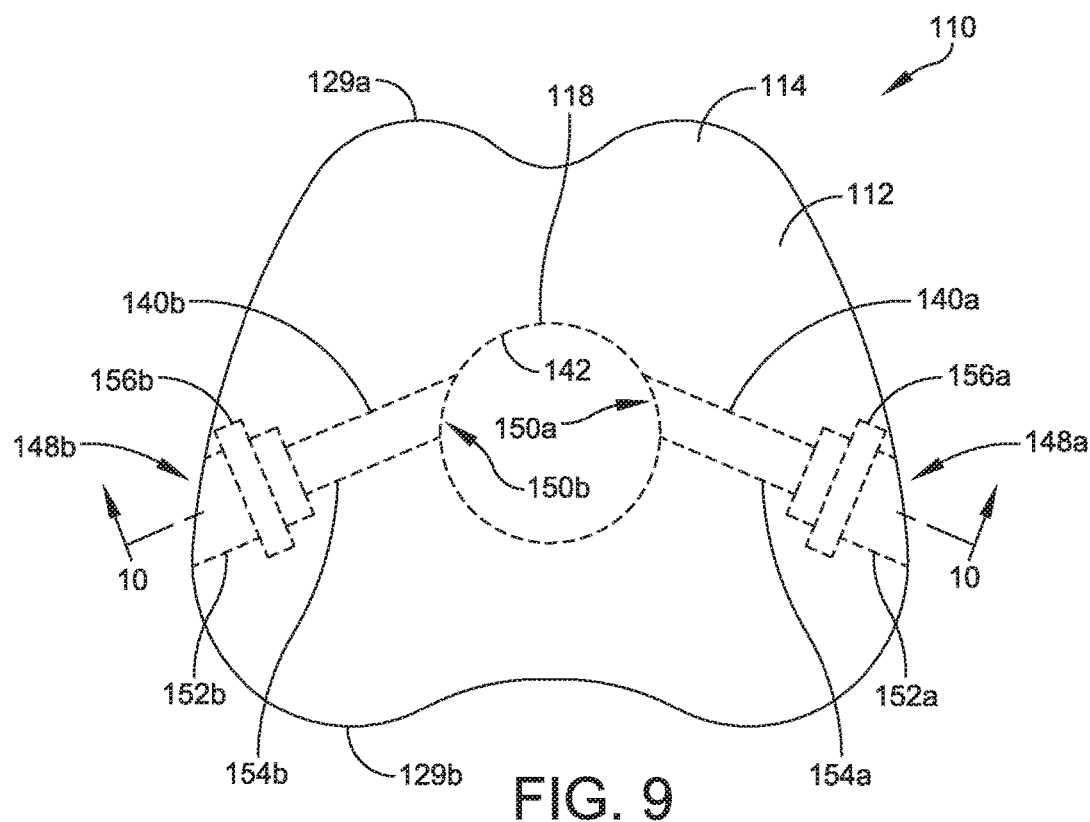
FIG. 9 illustrates a bottom view of the talar dome of FIG. 7, in accordance with some embodiments.
Figure 10:
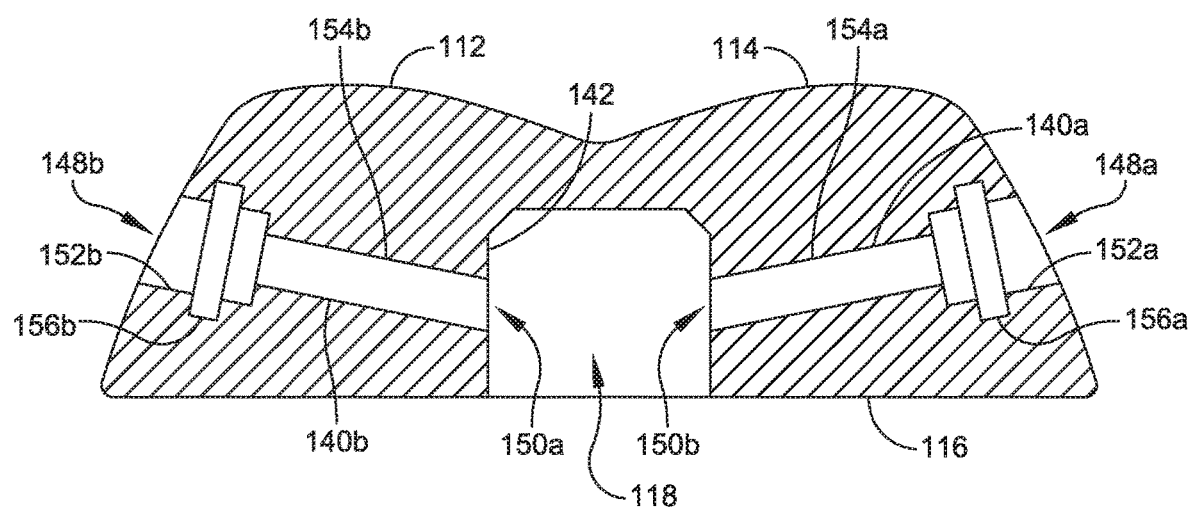
FIG. 10 illustrates a cross-sectional view of the talar dome taken along line 7-7 in FIG. 9, in accordance with some embodiments.

In some embodiments, the longitudinal axis 146a, 146b of each of the through holes 140a, 140b extends through the talar dome 110, 110a at an oblique angle with respect to the plate contact surface 116 of the talar dome 110 and/or an oblique angle with respect to an axis extending from an anterior edge 129a of the body 112 to a posterior edge 129b of the body 112. For example, and as shown in FIG. 9, in some embodiments, each of the through holes 140a, 140b have an opening 148a, 148b in the articulation surface 114 that is offset in a posterior direction with respect to an opening 150a, 150b formed in the interior wall 142 of the post hole 118. Similarly, and as shown in FIG. 10, in some embodiments, the opening 148a, 148b of each through hole 140a, 140b formed in the articulation surface 114 is positioned in a superior direction with respect to the holes 150a, 150b formed in the interior wall 142 of the post hole 118. Although embodiments are discussed herein with specific positions of the openings 148a, 148b, 150a, 150b, it will be appreciated that the superior/inferior, anterior/posterior, and/or medial/lateral position of each of the through holes 140a, 140b may be adjusted.

In some embodiments, each of the through holes 140a, 140b includes a first portion 152a, 152b having a first diameter and a second portion 154a, 154b having a second diameter that is equal to or less than the first diameter. The first portion 152a, 152b of each of the respective through holes 140a, 140b is sized and configured to receive a head portion of a fastener and the second portion 154a, 154b is sized and configured to receive a shaft or coupling portion of the fastener therein (as discussed in greater detail with respect to FIGS. 17-18).

In some embodiments, each of the through holes 140a, 140b defines a groove 156a, 156b extending at least partially circumferentially about the respective through hole 140a, 140b. Each of the grooves 156a, 156b includes an outer diameter larger than the first diameter and/or the second diameter of the through holes 140a, 140b. In the illustrated embodiment, each of the grooves 156a, 156b are positioned circumferentially about a first portion 152a, 152b of each of the respective through holes 140a, 140b and include an outer diameter greater than the first diameter of the through holes 140a, 140b, although it will be appreciated that the grooves 156*a*-156*b* can be located circumferentially about the second portion 154*a*, 154*b* of each through hole 140*a*, 140*b* and can have a diameter greater than the second portion 154*a*, 154*b* but less than the first portion 152*a*, 152*b*. Each groove 156*a*, 156*b* is sized and configured to receive a clip therein, as discussed in greater detail below.

The through holes 140*a*, 140*b* in the talar dome 110, 110*a* are configured to align with the fastener holes 132*a*, 132*b* formed in the post 130 when the post 130 is inserted into the post hole 118 and the talar dome 110, 110*a* is properly aligned with the talar plate 120. For example, in some embodiments, a central longitudinal axis of each of the through holes 140*a*, 140*b* is aligned with a central longitudinal axis of each of the fastener holes 132*a*, 132*b* in the post 130 when the post 130 is inserted into the post hole 118. As discussed above, in some embodiments, the post hole 118 and/or the post 130 include a geometry configured to allow insertion of the post 130 into the post hole 118 only in a predetermined alignment. The predetermined alignment corresponds to the through holes 140*a*, 140*b* and the post holes 132 being aligned. In other embodiments, the talar dome 110, 110*a* can rotate at least partially on the post 130 to allow the through holes 140*a*, 140*b* to be brought into alignment with the fastener holes 132*a*, 132*b*.

Figure 4:
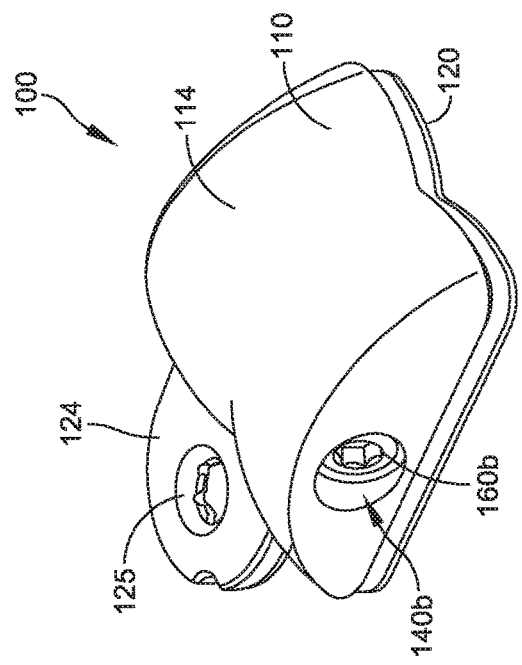
FIG. 4 illustrates a side perspective view of the talar implant of FIG. 3, in accordance with some embodiments.
Figure 6:
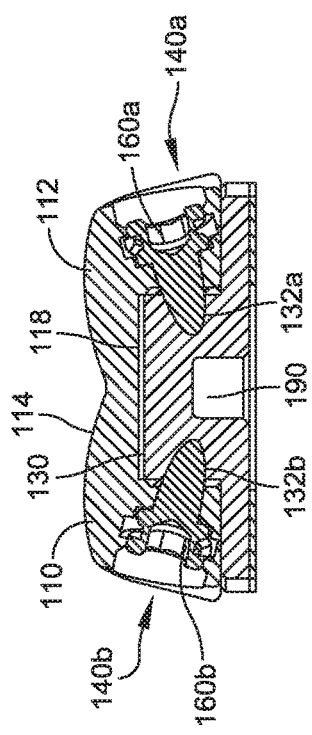
FIG. 6 illustrates a cross-sectional view of the talar implant taken along line 6-6 in FIG. 5, in accordance with some embodiments.
Figure 3:
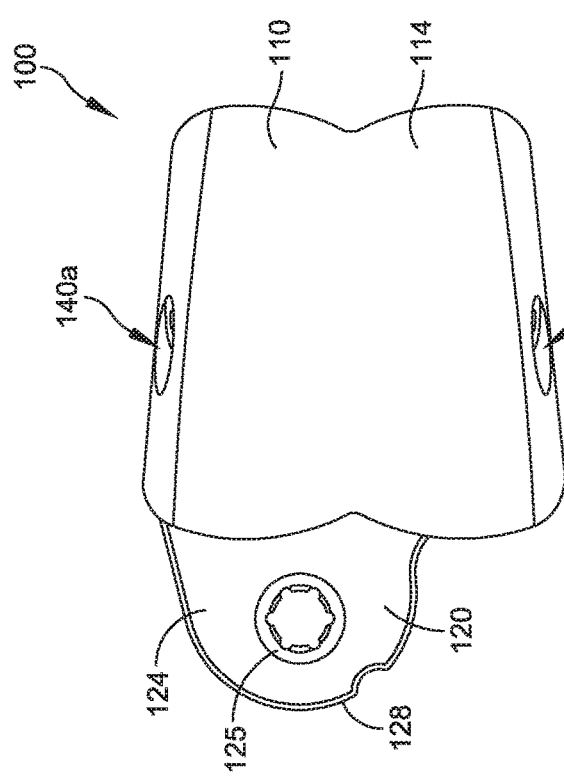
FIG. 3 illustrates a top view of a talar implant including a talar dome and a talar plate, in accordance with some embodiments.
Figure 5:
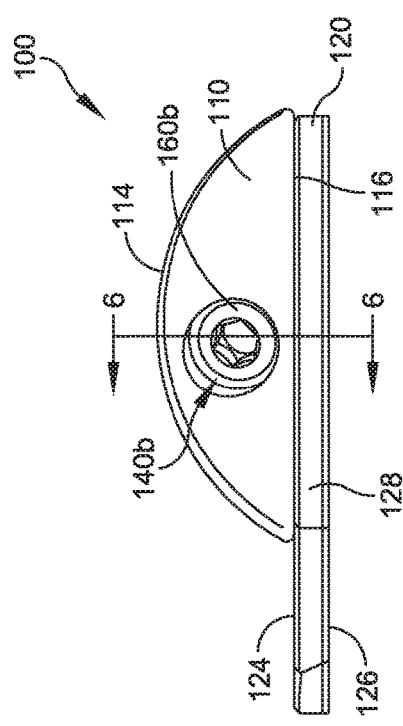
FIG. 5 illustrates a side view of the talar implant of FIG. 3, in accordance with some embodiments.
Figure 7:
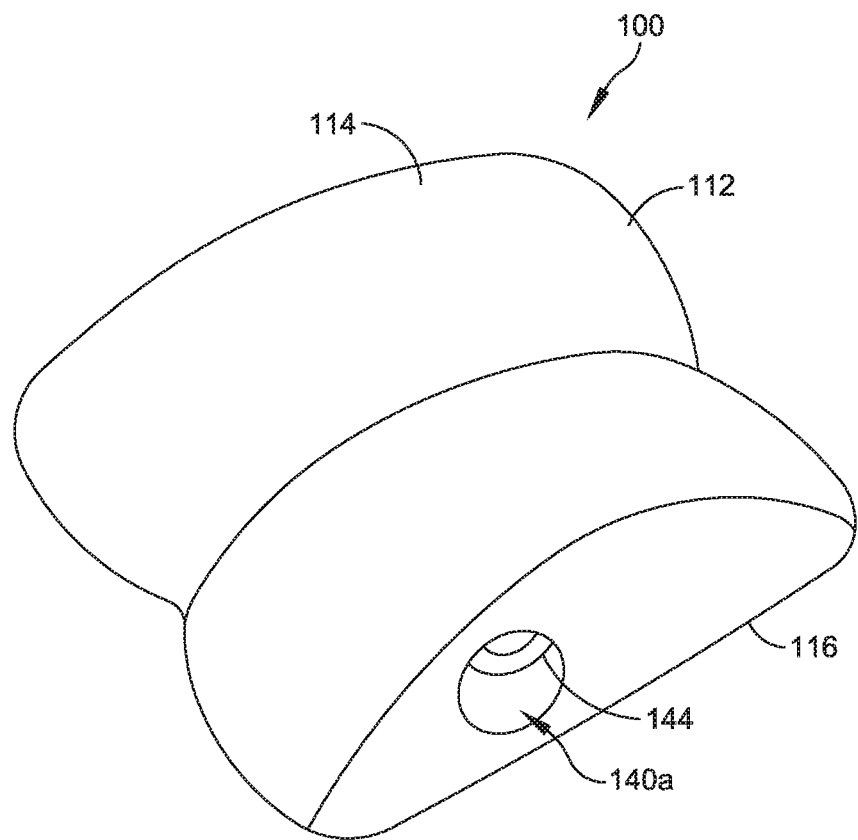
FIG. 7 illustrates a top perspective view of a talar dome defining at least one through hole, in accordance with some embodiments.
Figure 8:
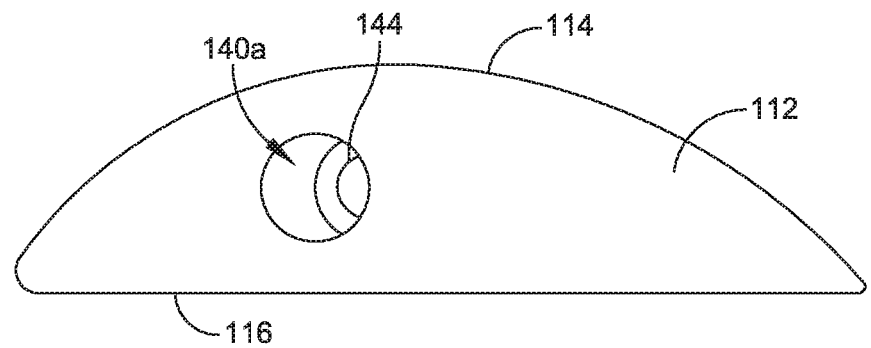
FIG. 8 illustrates a side view of the talar dome of FIG. 7, in accordance with some embodiments.

As illustrated in FIGS. 4-6, in some embodiments, one or more fasteners 160*a*, 160*b* are sized and configured to be inserted into the through holes 140*a*, 140*b* and the fastener holes 132*a*, 132*b*. FIG. 13 illustrates one embodiment of a fastener 160*c*, in accordance with some embodiments. Each fastener 160*a*-160*c* is configured to engage the threads 136 of a respective fastener hole 132*a*, 132*b* and/or the threads 144 of a respective through hole 140*a*, 140*b*.

Each fastener 160*a*-160*c* includes a head 162 having a first diameter and a shaft 164 coupled to and extending from the head 162. The shaft 164 extends substantially along a longitudinal axis from a first end 161*a* located adjacent to the head 162 to a second end 161*b* and has a second diameter. The first diameter of the head 162 may be greater than, less than, or equal to the second diameter of the shaft 164. The first diameter of the head 162 may be substantially equal to or slightly smaller than the diameter of the first portion 152*a*, 152*b* of the through holes 140*a*, 140*b* and the second diameter may be substantially equal to or slightly smaller than diameter of the second portion 154*a*, 154*b* of a through hole 140*a*, 140*b*. In some embodiments, the head 162 defines a tool cavity 166 extending from the first end 161*a* into the head 162. The tool cavity 166 is sized and configured to receive a driving tool therein.

In some embodiments, each fastener 160*a*-160*c* includes a groove 168 sized and configured to receive a clip therein. The groove 168 may be formed at least partially circumferentially about the head 162 of the fastener 160*a*-160*c*. Although embodiments are illustrated with a curved (or circular) circumferential groove 168, it will be appreciated that the circumferential groove 168 can include any suitable shape, such as, for example, circular, hexagonal, etc. In some embodiments, the groove 168 is positioned on the head 162 such that the groove 168 is aligned with the groove 154*a*, 154*b* of a respective through hole 140*a*, 140*b* when the fastener 160*a*-160*c* is fully inserted into a through hole 140*a*, 140*b* and a fastener hole 132*a*, 132*b*.

As illustrated in FIGS. 4-6, in some embodiments, a clip 180*a*, 180*b* is coupled to each of the fasteners 160*a*, 160*b*. FIGS. 14-15 illustrate one embodiment of a clip 180*c* including a retaining ring, in accordance with some embodiments. FIG. 16 illustrates one embodiment of a C clip 180*d*, in accordance with some embodiments. Each clip 180*a*-180*d* is sized and configured to be received at least partially within a groove 168 of a fastener 160*a*-160*c* and/or a groove 156*a*, 156*b* of a through hole 140*a*, 140*b*.

In some embodiments, a clip 180*a*-180*d* is configured to be coupled to a fastener 160*a*-160*c* prior to coupling the fastener 160*a*-160*c* to a talar implant 100. The clip 180*a*-180*d* is inserted into the groove 166 formed in the head 162 of the fastener 160*a*-160*c*. In some embodiments, the clip 180*a*-180*d* includes at least one chamfer. For example, in some embodiments, a first side 182 of the clip can include a first chamfer configured to interact with a circumferential inner wall of a through hole 140*a*, 140*b*. In some embodiments, a clip 180*d* can include a first chamfer on a top surface and a second chamfer on a bottom surface. As discussed in greater detail below, in some embodiments, the clip 180*a*-180*d* is configured to prevent removal of a fastener 160*a*-160*c* from a talar dome 110, 110*a*.

Figure 17:
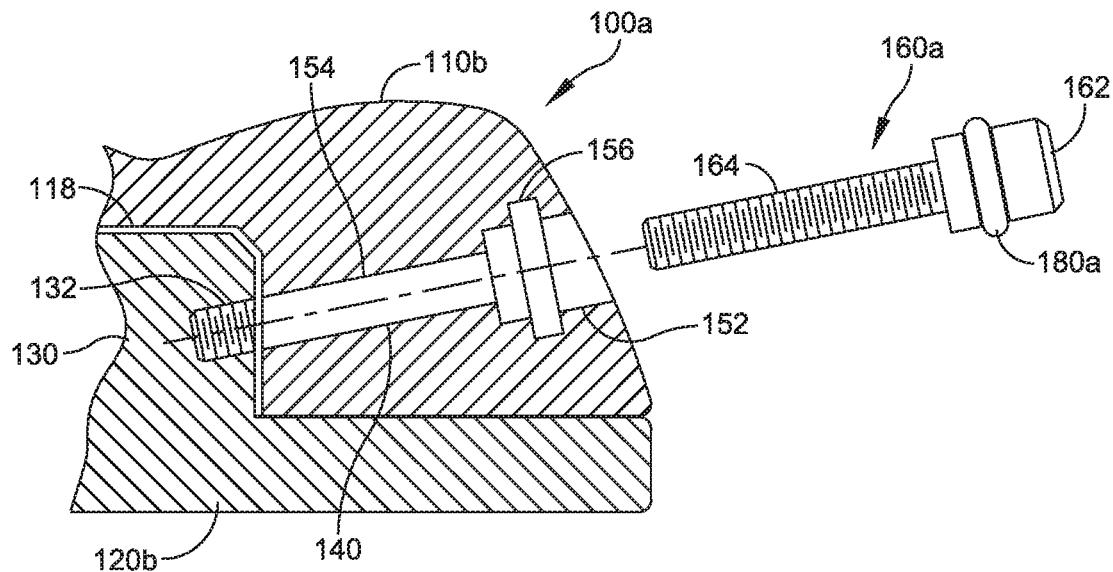
FIG. 17 illustrates a cross-sectional view of a talar implant including a plate, talar dome, screw, and clip, in accordance with some embodiments.
Figure 18:
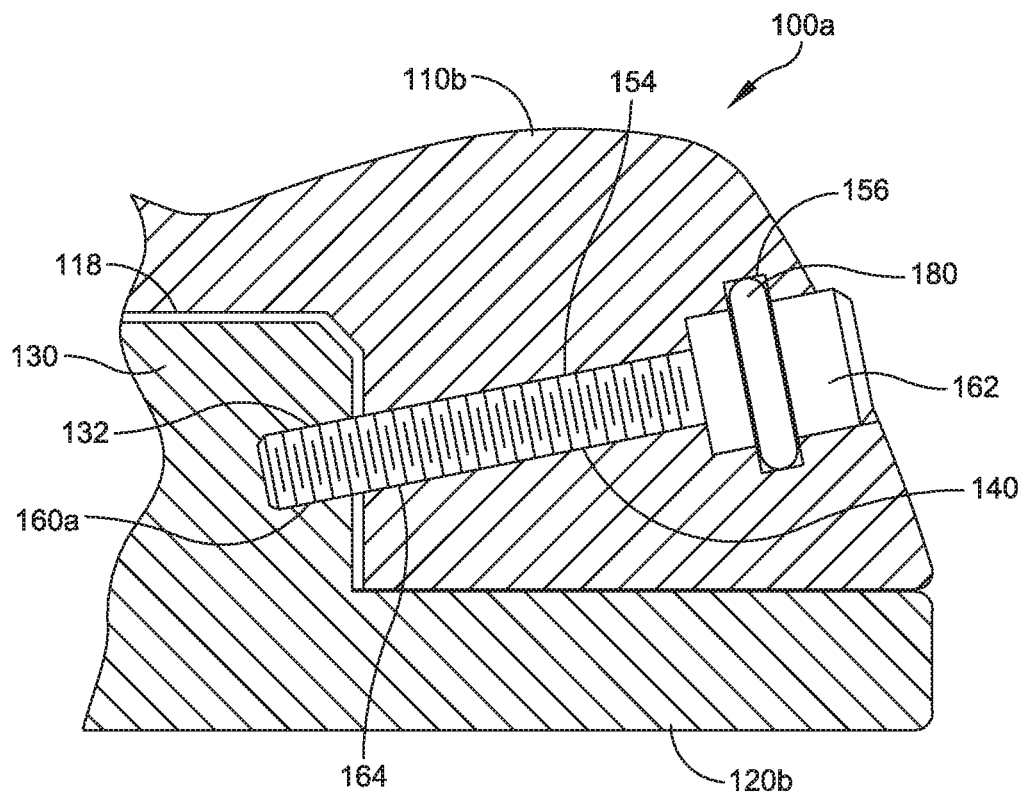
FIG. 18 illustrates the talar implant of FIG. 17 with the screw inserted into the talar dome and the post of the talar plate, in accordance with some embodiments.
Figure 19:
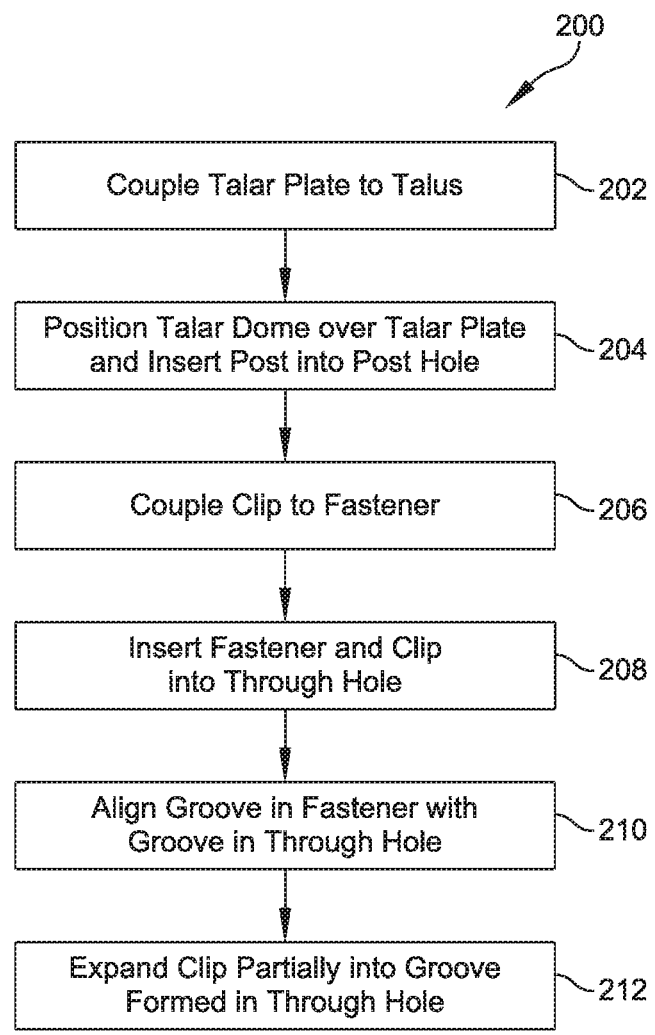
FIG. 19 illustrates a method of installing a talar implant, in accordance with some embodiments.

FIGS. 17-18 illustrate a process of coupling a talar dome 110*b* to a talar plate 120*b* using a first fastener 160*d*, in accordance with some embodiments. FIG. 19 is a flowchart illustrating a method 200 of inserting a talar implant 100*a*, in accordance with some embodiments. The talar dome 110*b*, talar plate 120*b*, and fastener 160*d* are similar to the talar domes 110, 110*a*, talar plates 120, 120*a*, and fasteners 160*a*-160*c* previously described and similar description is not repeated herein.

At step 202, the talar plate 120*b* is attached to a talus. For example, in some embodiments, the talar plate 120*b* can be coupled to a talus having a resected surface formed specifically for insertion of the talar plate 120*b* and/or during a prior ankle revision surgery. The talar plate 120*b* is inserted such that the inferior surface 126 of the talar plate 120*b* abuts the talus. At step 204, a talar dome 110*b* is placed over the talar plate 120*b*. The talar dome 110*b* is positioned such that the inferior surface 116 of the talar dome 110*b* abuts the superior surface 114 of the talar plate 120*b*. The post hole 118 formed in the inferior surface 116 of the talar dome 110*b* receives the post 130 of the talar plate 120*b*. In some embodiments, the talar dome 110*b* is positioned over the talar plate 120*b* without applying an impact force.

At step 206, a clip 180*e* is coupled to a fastener 160*d*. The clip 180*e* is sized and configured to be received within a groove 166 defined about at least a portion of the circumference of the head 162 of the fastener 160*d*. In some embodiments, the clip 180*e* can include a C clip and/or a retaining ring. At step 208, the fastener 160*d* is inserted into the through hole 140*a* to engage a threaded fastener hole 132*a* formed in the post 130 of the talar plate 120*b*. The threads 170 of the fastener 160*d* couple to the threads 136 of the fastener hole 132*a*. In some embodiments, the through hole 140*a* includes threads 146 configured to engage a portion of the threads 170 of the fastener 160*d*.

At step 210, the fastener 160*d* is fully inserted into the through hole 140*d* such that the head 162 of the fastener 160*d* is flush with and/or recessed beneath the articulation surface 114 of the talar dome 110*b*. When the fastener 160*d* is inserted into the through hole 140*a*, the clip 180*e* is compressed into the groove 168 by a force applied by the through hole 140*a*. In some embodiments, a chamfer formed on one or more surfaces of the clip 180*e* facilitate compression of the clip 180*e* by the wall of the through hole 140*a*. The clip 180*e* remains compressed in the groove 166 until the fastener 160*d* is fully inserted into the through hole 140*a*. At step 212, when the groove 166 in the fastener 160*d* is aligned with the groove 156 in the through hole 140*a*, the clip 180*e* expands from a compressed state to a partially compressed and/or uncompressed state. A portion of the clip 180e is positioned in the groove 156 and a portion of the clip 180e remains in the groove 166 of the fastener 160d. The clip 180e applies an additional force to maintain the fastener 160d in a fixed position with respect to the talar dome 110b and the talar plate 120b.

In some embodiments, and as discussed above, the through hole 140a and/or the fastener hole 132a can include longitudinal axes oriented at an oblique angle with respect to an inferior surface 116 of the talar dome 110b and/or can be offset from a central vertical axis of the post 130 such that the longitudinal axes do not extend through the central vertical axis of the post 130. In such embodiments, when the fastener 160d is inserted into the through hole 140a and the fastener hole 132a, a longitudinal axis of the fastener 160d is oriented at an oblique angle with respect to the inferior surface 116 of the talar dome 110b and/or does not extend through the central vertical axis of the post 130. Steps 206-210 may be repeated for one or more additional fasteners, although it will be appreciated that a single fastener 160d may be used in some embodiments.

Although the subject matter has been described in terms of exemplary embodiments, it is not limited thereto. Rather, the appended claims should be construed broadly, to include other variants and embodiments, which may be made by those skilled in the art.

What is claimed is:

1. A talar implant, comprising:
    a plate having an inferior surface configured for attachment to a talus, the plate having a post projecting from a superior surface of the plate, the post having at least one threaded hole;
    a talar dome having an inferior surface configured to face the plate, and an opening in the inferior surface shaped to receive the post, the talar dome having at least one through hole, the through hole having a threaded surface and a groove, the groove having a larger outer diameter than the threaded surface;
    at least one fastener configured to engage the threaded hole of the post and the threaded surface of the through hole, the at least one fastener having a groove that is aligned with the groove of the through hole when the fastener is inserted in the talar dome and the post; and
    at least one clip configured to engage the groove of the through hole of the talar dome and the groove of the fastener.

2. The talar implant of claim 1, wherein the at least one through hole has a longitudinal axis that is oriented at an oblique angle with respect to the inferior surface of the talar dome.

3. The talar implant of claim 2, wherein the post has a central vertical axis, and the longitudinal axis of the at least one through hole does not extend through the central vertical axis.

4. The talar implant of claim 1, wherein the at least one fastener has a head, the head having a larger diameter than the threaded surface, and the groove of the fastener is located on a circumferential surface of the head.

5. The talar implant of claim 1, wherein the at least one clip is a C clip.

6. The talar implant of claim 5, wherein the C clip has at least one chamfer.

7. The talar implant of claim 5, wherein the C clip has first and second chamfers on top and bottom surfaces thereof.

8. The talar implant of claim 1, wherein the at least one clip is a retaining ring.

9. The talar implant of claim 1, wherein the at least one clip is configured to prevent removal of the fastener from the talar dome while the clip engages the groove of the through hole and the groove of the fastener.

10. An ankle prosthesis comprising:
    a tibial component configured for attachment to a tibia of a person;
    a plate having an inferior surface configured for attachment to a talus of the person, the plate having a post projecting from a superior surface of the plate, the post having first and second threaded holes;
    a talar dome having an articulating surface configured to face the tibial component, an inferior surface configured to face the plate, and an opening in the inferior surface shaped to receive the post, the talar dome having first and second through holes, the first and second through holes having respective first and second threaded surfaces with a diameter and first and second grooves, respectively, the first and second grooves having an outer diameter larger than the diameter of the first and second threaded surfaces;
    first and second fasteners configured to engage the first and second threaded holes, and the first and second threaded surfaces of the talar dome, respectively, the first and second fasteners each having a groove that is aligned with the first and second grooves of the talar dome, respectively, when the first and second fasteners are inserted in the talar dome and the post; and
    first and second clips configured to engage the first and second grooves of the first and second through holes and the first and second grooves of the first and second fasteners, respectively.

11. The ankle prosthesis of claim 10, wherein each of the first and second through holes has a respective longitudinal axis that is oriented at an oblique angle with respect to the inferior surface of the talar dome.

12. The ankle prosthesis of claim 11, wherein the post has a central vertical axis, and the longitudinal axes of the first and second through holes do not extend through the central vertical axis.

13. The ankle prosthesis of claim 10, wherein the first and second fasteners have first and second heads, respectively, the first and second heads having a larger diameter than the first and second threaded surfaces, and the first and second grooves of the first and second fasteners are located on respective circumferential surface of the first and second heads.

14. The ankle prosthesis of claim 10, wherein each of the first and second clips is a C clip having top and bottom chamfers on top and bottom surfaces thereof.

* * * * *